United States Patent [19]
Voges et al.

[11] Patent Number: 6,124,509
[45] Date of Patent: Sep. 26, 2000

[54] CATALYTIC IONIC HYDROGENATION OF KETONES USING TUNGSTEN OR MOLYBDENUM ORGANOMETALLIC SPECIES

[75] Inventors: Mark Voges, Leverkusen, Germany; R. Morris Bullock, Wading River, N.Y.

[73] Assignee: Brookhaven Science Associates, Upton, N.Y.

[21] Appl. No.: 09/235,207

[22] Filed: Jan. 22, 1999

[51] Int. Cl.[7] .................................................. C07C 29/14
[52] U.S. Cl. ........................... 568/881; 568/809; 568/814
[58] Field of Search .................................. 568/814, 881, 568/809

[56] References Cited

U.S. PATENT DOCUMENTS

| | | | |
|---|---|---|---|
| 4,940,819 | 7/1990 | Kiel et al. | 568/318 |
| 4,967,031 | 10/1990 | Bullock | 585/250 |
| 5,182,246 | 1/1993 | Fuchikami et al. | 502/161 |

OTHER PUBLICATIONS

Tatsumi T., Kizawa, K., Tominaga, H., "Homogeneous Transfer Hydrogenation of Kentones Catalyzed by Molybdenum Complexes," Chemical Society of Japan, Chemistry Letters 191–194 (1977).

Kitamura, M., Ohkuma, T., Inoue, S., Sayo, N., Kumobayashi, H., Akutagawa, S., Ohta, T., Takaya, H. Noyori, R., "Homogeneous Asymmetric Hydrogenation of Functionalized Ketones," *J. Am. Chem. Soc.*, 110:629–631 (1988).

Ohkuma, T., Ooka, H., Hashiguchi, S., Ikariya, T., Noyori, R., "Practical Enantioselective Hydrogenation of Aromatic Ketones," *J. Am Chem. Soc.*, 117: 267–2676 (1995).

Fujii, A., Hashiguchi, S., Uematsu, N., Ikariya, T. Noyori, R., "Ruthenium(II)–Catalyzed Asymmetric Transfer Hydrogenation of Ketones Using a Formic Acid–Triethylamine Mixture," *J. Am. Chem. Soc.*, 118: 2521–2522 (1996).

Zhang, X., Taketomi, T., Yoshizumi, T., Kumobayashi, H., Akutagawa, S., Mashima, K., Takaya, H., "Asymmetric Hydrogenation of Cycloalkanones Catalyzed by BINA-P–Ir(I)–Aminophosphine Systems," *J. Am. Chem. Soc.*, 115: 3318–3319 (1993).

Ohkuma, T., Ooka, H., Ikariya, T., Noyori, R., "Preferential Hydrogenation of aldhydes and Ketones," *J. Am. Chem. Soc.*, 117 10417–10418 (1995).

Shohei, H., Fujii, A., Takehara, J., Ikariya, T., Noyori, R., "Asymmertric Transfer Hydrogenation of Aromatic Ketones Catalyzed by Chiral Ruthenium(II) Complexes," *J. Am. Chem. Soc.*, 117: 7562–7563 (1995).

Mizushima, E., Yamaguchi, M., Yamagishi, T., "Effective Catalysts for Transfer Hydrogenation of Ketones and Imines by Propan–2–ol: Ruthenium–Dihydride Complexes," The Chemical Society of Japan, Chemistry Letters 1997, 237 (1997).

(List continued on next page.)

*Primary Examiner*—Michael L. Shippen
*Attorney, Agent, or Firm*—Margaret C. Bogosian

[57] ABSTRACT

The present invention is a process for the catalytic hydrogenation of ketones and aldehydes to alcohols at low temperatures and pressures using organometallic molybdenum and tungsten complexes. The functional group is selected from groups represented by the formulas R(C=O)R' and R(C=O)H, wherein R and R' are selected from hydrogen or any alkyl or aryl group. The active catalyst for the process has the form: $[CpM(CO)_2 (PR*_3) L]^+A^-$, where $Cp=\eta^5-R^{\blacktriangle}_mC_5H_{5-m}$ and $R^{\blacktriangle}$ represents an alkyl group or a halogen (F, Cl, Br, I) or $R^{\blacktriangle}=OR'$ (where R'=H, an alkyl group or an aryl group) or $R^{\blacktriangle}=CO_2R'$ (where R'=H, an alkyl group or an aryl group) and m=0 to 5; M represents a molybdenum atom or a tungsten atom; $R*_3$ represents three hydrocarbon groups selected from a cyclohexyl group ($C_6H_{11}$), a methyl group ($CH_3$), and a phenyl group ($C_6H_5$) and all three R* groups can be the same or different or two of the three groups can be the same; L represents a ligand; and $A^-$ represents an anion. In another embodiment, one, two or three of the R* groups can be an OR*.

13 Claims, 1 Drawing Sheet

OTHER PUBLICATIONS

Tooley, P.A. Ovalles, C., Kao, S.C., Darensbourg, D.J., Darensbourg, M.Y., "Anionic Group 6 Hydrides and Carboxylates as Homogeneous Catalysts for Reduction of Aldehydes and Ketones," *J. Am. Chem. Soc.*, 108:5465–5470 (1986).

Song, J–S., Szalda, D.J., Bullock, R.M., Lawrie, C.J.C., Rodkin, M.A., Norton, J.R., "Hydride Transfer by Hydrido Transition–Metal Complexes. Ionic Hydrogenation of Aldehydes and Ketones, and Structural Characterization of an Alcohol Complex," *Angewandte Chemie*, 31(9): 1233–1235 (1992).

Marko, L., Nagy–Magos, Z., "Homogeneous Hydrogenation of Ketones Using Chromium Hexacarbonyl as Catalyst Precusor in the Presence of Bases," *Journal of Organometallic Chemistry*, 285: 193–203 (1985).

Chalones, P.A., Esteruelas, M.A., Joo, F., Oro, L.A., "Homogeneous Hydrogenation," *Kluwer Academic Publishers*, 15: 28–29, 42–47, 80–83, 128–131, 162–169, 176–177, 180–181 (1994).

Fuchikami, T., Ubukata, Y., Tanaka, Y., "Group 6 Anionic $\mu$–Hydride Complexes $[HM_2(CO)_{10}]$–(M=Cr, Mo, W): New Catalysts for Hydrogenation and Hydrosilylation," *Tetrahedron Letters*, 32(9): 1199–1202 (1991).

CATALYTIC IONIC HYDROGENATION OF KETONES USING TUNGSTEN OR MOLYBDENUM ORGANOMETALLIC SPECIES

This invention was made with Government support under contract number DE-AC02-98CH10886, awarded by the U.S. Department of Energy. The Government has certain rights in the invention.

BACKGROUND OF THE INVENTION

The present invention relates to a process for the catalytic hydrogenation of unsaturated organic compounds that can be carried out at low temperatures and pressures. More specifically, the invention relates to a process for the hydrogenation of ketones and aldehydes to alcohols using organometallic tungsten (W) and molybdenum (Mo) complexes as catalysts.

Hydrogenation reactions involve the addition of hydrogen to an organic compound whereby, for example, a ketone can be reduced to an alcohol. Prior art processes have generally required the presence of a heterogeneous catalyst with a solid phase of platinum, rhodium, palladium or nickel along with relatively high hydrogen pressure and elevated temperature.

Traditional homogeneous catalysts for hydrogenation of ketones or aldehydes use precious metals such as rhodium (Rh), iridium (Ir) or ruthenium (Ru), which are extremely expensive and, therefore, frequently uneconomical. In contrast, the catalysts of the present invention, which use either molybdenum (Mo) or tungsten (W), are much less expensive to prepare, and, thus, offer economic advantages.

SUMMARY OF THE INVENTION

The present invention provides a process for the homogeneous catalytic hydrogenation of ketones to alcohols using $H_2$ as the stoichiometric redundant and organometallic tungsten (W) and molybdenum (Mo) complexes as the catalysts.

The homogeneous organometallic Mo and W complexes of the present invention provide an effective hydrogenation catalyst at a considerably reduced cost over the prior art catalysts that use Rh (rhodium), Ir (iridium) and Ru (ruthenium) complexes.

The present invention is a process for the catalytic hydrogenation of an organic compound which contains at least one reducible functional group. The process is particularly well suited to the hydrogenation of ketones and aldehydes. The functional group is selected from groups represented by the formulas R(C=O)R' and R(C=O)H, wherein R and R' are selected from hydrogen (H) or any alkyl or aryl group. R and R' can both be selected from H or from an alkyl group or from an aryl group, and can be the same or different.

The process includes the steps of reacting the organic compound in the presence of hydrogen with a catalyst made up of an organometallic complex that includes a metal selected from tungsten and molybdenum. The organometallic complex used for the catalyst is represented by the formula: $[CpM(CO)_2(PR^*_3)L]^+A^-$; wherein $Cp=\eta^5-R^{\blacktriangle}_mC_5H_{5-m}$ and $R^{\blacktriangle}$ represents an alkyl group or a halogen (F, Cl, Br, I) or $R^{\blacktriangle}=OR'$ (where R'=H, an alkyl group or an aryl group) or $R^{\blacktriangle}=CO_2R'$ (where R'=H, an alkyl group or an aryl group) and m=0 to 5; M represents a molybdenum atom or a tungsten atom; $R^*_3$ represents three hydrocarbon groups selected from a cyclohexyl group ($C_6H_{11}$), a methyl group ($CH_3$), and a phenyl group ($C_6H_5$) and all three R* groups can be the same or different or two of the three groups can be the same; L represents a ligand; and $A^-$ represents an anion. In another embodiment, one, two or three of the R* groups can be an OR*, that is any combination of $PR_n(OR')_{3-n}$, where n=0,1,2, or 3 and R and R' are the same or different and can be selected from H or any alkyl or aryl group.

The ligand can be the anion $A^-$, a solvent molecule, a ketone substrate molecule, a product alcohol molecule and can be a weakly coordinated ligand, such as a C=C bond of a $PPh_3$ ligand. The anion ($A^-$) can be $PF_6^-$, $BF_4^-$, $SbF_6^-$, $CF_3SO_3^-$ and $BAr'_4^-$, wherein Ar'=3,5-bis(trifluoromethyl)phenyl. The preferred solvent molecule is selected from a group that includes dichloromethane ($CH_2Cl_2$), toluene ($C_6H_5CH_3$), chlorobenzene ($ClC_6H_5$), trifluorotoluene ($CF_3C_6H_5$) or combinations of one or more of these solvents. The solvent molecule can also be the organic compound that is being hydrogenated.

The process is carried out in the presence of hydrogen at a pressure of from about 1 atmosphere to about 3 atmospheres and at a temperature above about 0° C., and preferably above about 20° C. Temperatures above about 20° C. are preferred because at temperatures below 20° C. the reactions are very slow.

The molybdenum and tungsten catalyst complexes of the present invention provide significant cost advantages over prior art processes which use expensive rhodium, iridium and ruthenium catalyst complexes. The less expensive catalysts of the present invention make it practical to hydrogenate organic compounds in commercial operations that previously had not been economically feasible.

DETAILED DESCRIPTION OF THE PREFERRED EMBODIMENTS

Figure 1:
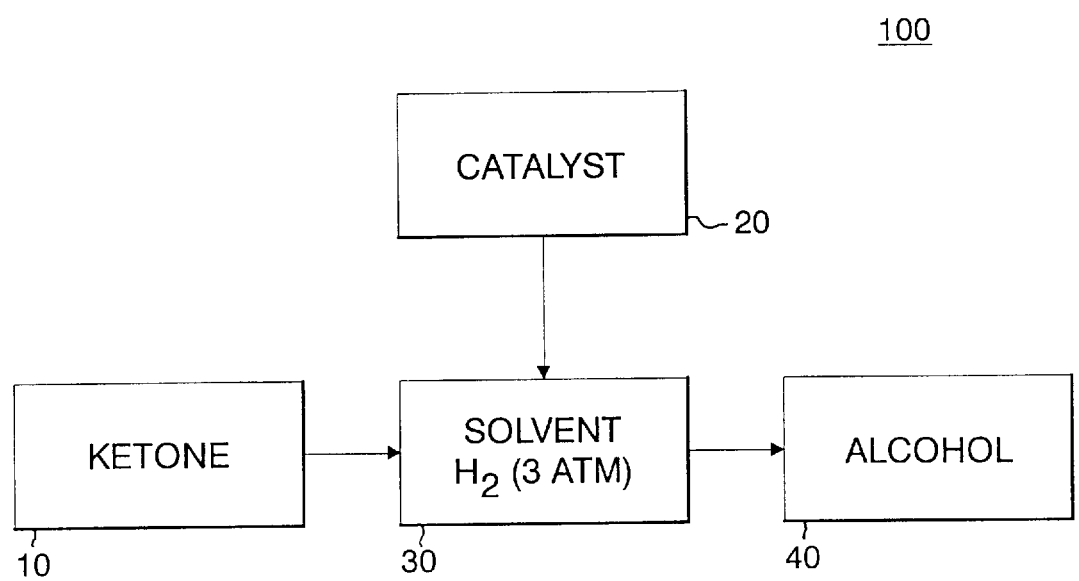
FIG. 1 shows a block diagram of the process of the present invention.

The process described herein can be used for a variety of hydrogenation reactions. As used herein, hydrogenation means the reaction of hydrogen with an organic compound, and encompasses processes that can also be called reduction, whereby electrons are accepted by a compound and hydrogen is added to a compound.

The present invention provides a process for hydrogenating ketones and aldehydes to alcohols using organometallic molybdenum and tungsten complexes as the catalysts. Using the process of this invention, unsaturated organic compounds can be hydrogenated to give the corresponding saturated derivatives. Organic compounds which may be hydrogenated in accordance with the present invention include but are not limited to ketones and aldehydes. The hydrogenation of ketones and aldehydes involves the overall addition of two hydrogen atoms to the carbon-oxygen double bond to result in the formation of the corresponding alcohol.

CATALYSTS

The active organometallic catalyst for the present invention is prepared by using a hydride abstracting agent to remove a hydride from a transition metal hydride. The transition metal hydride has the form: $CpM(CO)_2(PR^*_3)H$, where $Cp=\eta^5-C_5H_5$, M=Mo or W, and R*=Cy (cyclohexyl, $C_6H_{11}$), Me (methyl, $CH_3$) or Ph (phenyl, $C_6H_5$).

The hydride abstracting agent can have the form: $Ph_3C^+ A^-$, where $A^-$ is an anion. The hydride removal produces an active catalyst having the form: [Cp M $(CO)_2(PR^*_3)$ L]+A$^-$, where L is a weakly coordinating ligand. The weakly coordinating ligand can be the anion A$^-$, a solvent molecule, a ketone substrate molecule, a product alcohol molecule, or a C=C bond of a PPh$_3$ ligand. Anions (A$^-$) shown to be effective include PF$_6^-$, BF$_4^-$, OTf$^-$, where OTf=CF$_3$SO$_3$ and BAr'$_4^-$ (where Ar'=3,5-bis(trifluoromethyl)phenyl). Solvents of moderate polarity can be used, including the ketone to be hydrogenated. A preferred solvent is CH$_2$Cl$_2$ (dichloromethane).

The active catalyst can either be prepared and isolated, or generated in situ. The turnover rate (i.e., the number of moles of ketone hydrogenated per mole of catalyst per unit of time) depends on the metal, the phosphine, and the counterion employed. Catalysis occurs at room temperature (23° C.) and low pressures of H$_2$ (3 atmospheres) but can also be carried out at higher temperatures and pressures.

Example of Catalyst Preparation

A catalyst used for the present invention was synthesized by combining 288.5 mg (0.26 mmol) of Ph$_3$C$^+$BAr'$_4^-$, a hydride abstracting agent, and 0.10 mL (0.95 mmol) of Et$_2$CO (diethyl ketone or 3-pentanone) in a flask under argon. 8 mL of CH$_2$Cl$_2$ solvent, dichloromethane, was then added to form a yellow solution. 148.5 mg (0.26 mmol) of CpW(CO)$_2$(PPh$_3$)H, a transition metal hydride, was stirred into the yellow solution and formed a red-orange solution. After 5 minutes of additional stirring, 30 mL of hexane (CH$_3$(CH$_2$)$_4$CH$_3$) was slowly added until the solution became cloudy and a reddish-orange precipitate oiled out of solution. The solution was left standing at room temperature and, within a few minutes, the oil solidified into small microcrystals. This orange-red solid was collected by filtration, and washed three times with 5 mL of hexane to yield 354 mg (0.23 mmol, 88%) of active catalyst.

The complex formed by the synthesis was characterized by $^1$H, $^{13}$C, and $^{31}$P Nuclear Magnetic Resonance spectroscopy, Infrared spectroscopy and elemental analysis. The equation showing the synthesis of the [CpW(CO)$_2$(PPh$_3$)(Et$_2$CO)]$^+$BAr'$_4^-$ active catalyst is shown below in formula (1):

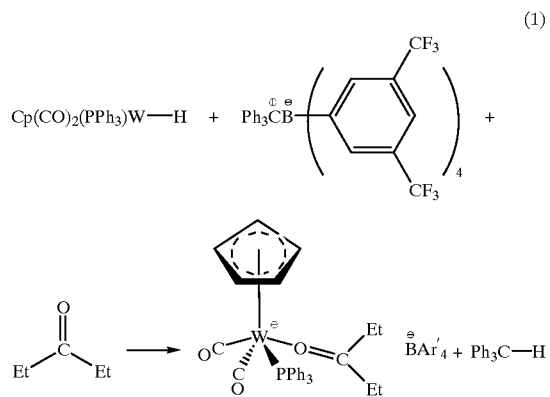

(1)

The catalyst precursors of the present invention have the general formula

[CpM(CO)$_2$(PR*$_3$)L]$^+$A$^-$     (2)

where M=Mo or W, R*=CH$_3$, Ph (Ph=C$_6$H$_5$), or Cy (Cyclohexyl, C$_6$H$_{11}$), L is a ligand (such as a ketone) and A$^-$=PF$_6^-$, BF$_4^-$, SbF$_6^-$, OTf$^-$ (OTf=CF$_3$SO$_3$), or BAr'$_4^-$ [Ar'=3,5-bis(trifluoromethyl)phenyl].

The ligand shown above in formula (2) can be a ketone selected from ketones having the general formula R(C=O)R', where R and R' may or may not be the same, and each can be hydrogen (H) or any alkyl or aryl group. An aldehyde ligand can be used instead of a ketone ligand to form an active catalyst having the formula [CpM(CO)$_2$(PR*$_3$)(aldehyde)]$^+$A$^-$, where the aldehyde has the general formula, R(CO)H and R is selected from hydrogen (H) or from any alkyl or aryl group. In addition to phosphine (PR*$_3$) ligands, phosphite ligands [P(OR*)$_3$] can also be used or ligands that are a combination of both, such as, [P(R*)(OR*)$_2$] and [P(R*)$_2$(OR*)], where R* can be the same or different and can be either H or an alkyl or aryl group.

The hydrogenation reaction can take place at relatively low pressures compared to previously known catalytic hydrogenation processes. The process of the present invention can be carried out over a wide range of hydrogen pressures. However, at hydrogen pressures below 1 atmosphere, the reaction rates are relatively slow and, therefore, hydrogen pressures at or above 1 atmosphere are preferred. Experiments have been carried out at hydrogen pressures as high as 65 atmospheres and the results show that pressures above 65 atmospheres can also be used. The preferred hydrogen is about 3 atmospheres.

Along with complexes having ketone ligands, related compounds are also suitable catalyst precursors, including dihydride complexes having two metal-hydrogen bonds and the form MH$_2^+$ (see example #9), metal triflates (see example #10), and complexes containing a FBF$_3$ ligand (see example #11).

The ketone complex can be prepared and isolated and then used as a catalyst. The hydride can also be removed from a metal hydride in the presence of an excess amount of ketone to generate the catalytically active species in the reaction directly (examples #3 and #12). Example #8 shows a case where the catalyst precursor is a complex containing a weakly bound ligand, dichloromethane (CH$_2$Cl$_2$). The ketone rapidly displaces the dichloromethane under the conditions of the experiment.

FIG. 1 shows an example of the process 100 for the present invention. A ketone 10 and a catalyst 20 are added to a solvent 30 in the presence of hydrogen pressurized to 3 atmospheres to produce an alcohol 40. A typical reaction of the present invention for the hydrogenation of diethyl ketone (3-pentanone) to 3-pentanol (Et=C$_2$H$_5$) is shown in Equation 3.

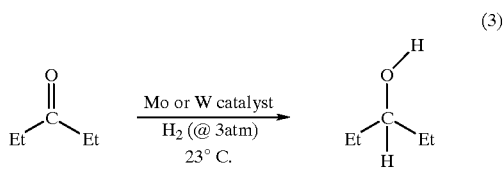

(3)

For many of the reactions, the alcohol formed by the hydrogenation reaction undergoes further reaction and produces the corresponding ether and one equivalent of water, as shown below:

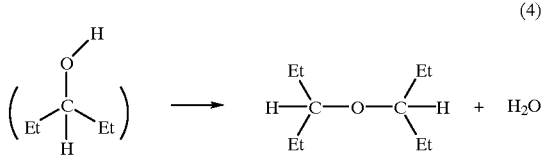

(4)

The reactions of the present invention are preferably carried out in a liquid phase, that is, reaction components are dissolved in an organic solvent. Any solvent which is chemically inert, which does not interfere with the hydrogenation reaction and which at least partially dissolves the catalyst may be employed. The solvents may be paraffinic, preferably having 5 through 20 carbons such as pentane, heptane, octane, etc.; $C_6$ through $C_{12}$ aromatics such as toluene, xylene, mesitylene and benzene; or halogenated aromatics. Preferred solvents are dichloromethane (methylene chloride, $CH_2Cl_2$) and toluene ($C_6H_5CH_3$). If the reactants are mutually soluble, the use of a solvent is not necessary. In addition, the substrate, either a ketone or an aldehyde, can be partially soluble or it can be completely soluble in the solvent.

The hydrogenation process of the invention can be carried out over a wide range of temperatures, with the primary limiting factor being the freezing or boiling point of the solvent and reactants. A preferred temperature range is from about −95° C. to about 60° C., with a range of about 0° C. to about 25° C. most preferred for the sake of convenience.

The process can be carried out at ambient pressure and in any type of apparatus which enables intimate contact of the reactants and control of operating conditions. The hydrogenated product may be removed by known means such as distillation and chromatography.

EXAMPLES

In the experiments described below, each equivalent of ether is counted as representing two hydrogenation equivalents (or turnovers of the catalyst), since it takes two alcohols to form one ether. The invention can be illustrated by the following examples:

Example 1

A solution of 30 mM of $[CpW(CO)_2(PPh_3)(Et_2CO)]^+$ $BAr'_4^-$ and 300 mM of 3-pentanone (diethyl ketone, $C_2H_5COC_2H_5$) in $CD_2Cl_2$ solvent under $H_2$ (3 atm) was allowed to react at 22° C. The progress of the reaction was periodically monitored by $^1H$ Nuclear Magnetic Resonance (NMR) and $^{31}P$ NMR spectroscopy. After 24 days, $Et_2CHOH$ (3-pentanol) had formed (93 mM, 3.1 turnovers). In addition, 5.7 mM of the ether $(Et_2CH)_2O$ had formed, representing an additional 0.38 turnovers, for a total of 3.5 catalyst turnovers.

Example 2

A solution of 30 mM of $[CpW(CO)_2(PMe_3)(Et_2CO)]^+$ $BAr'_4^-$ and 300 of mM 3-pentanone (diethyl ketone, $C_2H_5COC_2H_5$) in $CD_2Cl_2$ solvent under $H_2$ (3 atm) was allowed to react at 22° C. The progress of the reaction was periodically monitored by $^1H$ NMR and $^{31}P$ NMR spectroscopy. After 16 days, 69 mM (2.3 turnovers) of $Et_2CHOH$ (3-pentanol) had formed.

Example 3

A $CD_2Cl_2$ solution (0.7 mL) containing 300 mM of 3-pentanone (diethyl ketone, $C_2H_5COC_2H_5$) was added to an NMR tube containing $CpW(CO)_2(PCy_3)H$ (12.4 mg, 0.021 mmol) and $Ph_3C^+BAr'_4^-$ (23.2 mg, 0.021 mmol). This gave a solution that was 30 mM in the W (tungsten) catalyst. This red solution was cooled to −196° C., and $H_2$ was added, giving about 3 atm when the solution was warmed to 22° C. The progress of the reaction was periodically monitored by $^1H$ NMR and $^{31}P$ NMR spectroscopy. After 20 days, $Et_2CHOH$ (3-pentanol) had formed (129 mM, 4.3 turnovers). In addition, 2.2 mM of the ether $(Et_2CH)_2O$ had formed, representing an additional 1.1 turnovers, for a total of 5.4 catalyst turnovers.

Example 4

A solution of 30 mM of $[CpMo(CO)_2(PPh_3)(Et_2CO)]^+$ $BAr'_4^-$ and 300 mM of 3-pentanone (diethyl ketone, $C_2H_5COC_2H_5$) in $CD_2Cl_2$ solvent under $H_2$ (3 atm) was allowed to react at 22° C. The progress of the reaction was periodically monitored by $^1H$ NMR and $^{31}p$ NMR spectroscopy. After 5 days, the reaction was over 90% complete, and $Et_2CHOH$ (3-pentanol) had formed (236 mM, 7.9 turnovers). In addition, 35 mM of the ether $(Et_2CH)_2O$ had formed, representing an additional 2.4 turnovers, for a total of 10.3 catalyst turnovers.

Example 5

A solution of 30 mM of $[CpMo(CO)_2(PMe_3)(Et_2CO)]^+$ $BAr'_4^-$ and 300 mM of 3-pentanone (diethyl ketone, $C_2H_5COC_2H_5$) in $CD_2Cl_2$ solvent under $H_2$ (3 atm) was allowed to react at 22° C. The progress of the reaction was periodically monitored by $^1H$ NMR and $^{31}P$ NMR spectroscopy. After 24 days, $Et_2CHOH$ (3-pentanol) had formed (101 mM, 3.4 turnovers). In addition, 25 mM of the ether $(Et_2CH)_2O$ had formed, representing an additional 1.6 turnovers, for a total of 5.0 catalyst turnovers.

Example 6

A solution of 30 mM of $[CpW(CO)_2(PPh_3)(Et_2CHOH)]^+$ $BAr'_4^-$ and 300 mM 3-pentanone (diethyl ketone, $C_2H_5COC_2H_5$) in $CD_2Cl_2$ solvent under $H_2$ (3 atm) was allowed to react at 22° C. The progress of the reaction was periodically monitored by $^1H$ NMR and $^{31}P$ NMR spectroscopy. After 25 days, $Et_2CHOH$ (3-pentanol) had formed (95 mM, 3.2 turnovers, in addition to the 3-pentanol added as a ligand on the catalyst). In addition, 7.6 mM of the ether $(Et_2CH)_2O$ had formed, representing an additional 0.51 turnovers, for a total of 3.7 catalyst turnovers.

Example 7

A $CD_2Cl_2$ solution was added to an NMR tube containing 3.0 mg ($5.9 \times 10^{-3}$ mmol) of $CpMo(CO)_2(PCy_3)H$, 6.2 mg ($5.6 \times 10^{-3}$ mmol) of $Ph_3C^+BAr'_4^-$, and 0.060 mL (0.57 mmol) of 3-pentanone (diethyl ketone, $C_2H_5COC_2H_5$). This gave a solution (0.6 mL) that included about 10 mM of the Mo catalyst. This pink-red solution was cooled to −196° C., and $H_2$ was added to provide a pressure of about 3 atm when the solution was warmed to 22° C. The progress of the reaction was periodically monitored by $^1H$ NMR and 31P NMR spectroscopy. After 20 hours, a total of 28 turnovers was observed: $Et_2CHOH$ (3-pentanol) (22 turnovers) along with $(Et_2CH)_2O$ (6 turnovers).

Example 8

28.2 mg ($1.95 \times 10^{-2}$ mmol) of $[CpMo(CO)_2(PCy_3)(CH_2Cl_2)]^+BAr'_4^-$ was placed in an NMR tube, and 0.5 mL of a $CD_2Cl_2$ solution was added. 0.010 mL (0.095 mmol, ~5 equivalents) of 3-pentanone (diethyl ketone, $C_2H_5COC_2H_5$) was then added in the presence of $H_2$ (3 atm) and the solution was allowed to react at 22° C. After 2.5 hours, all of the ketone had been hydrogenated, producing the alcohol $Et_2CHOH$ (3-pentanol) and the ether $(Et_2CH)_2O$.

Example 9

35.3 mg (0.0283 mmol) of $[CpW(CO)_2(PMe_3)(H)_2]^+$ $BAr'_4{}^-$ was placed in an NMR tube, and 0.72 mL of $CD_2Cl_2$ was added. 0.011 mL (0.10 mmol, ~3.7 equivalents) of 3-pentanone (diethyl ketone, $C_2H_5COC_2H_5$) was then added in the presence of $H_2$ (3 atm) and the solution was allowed to react at 22° C. The progress of the reaction was periodically monitored by $^1H$ NMR and $^{31}P$ NMR spectroscopy. After 15 days, about 58% of the 3-pentanone had been hydrogenated, producing $Et_2CHOH$ (3-pentanol) (1.8 turnovers) and the ether $(Et_2CH)_2O$ (0.3 turnovers).

Example 12

5.2 mg (0.010 mmol) of $CpMo(CO)_2(PCy_3)H$, 3.9 mg (0.010 mmol) of $Ph_3C^+PF_6{}^-$, 3-pentanone (diethyl ketone, $C_2H_5COC_2H_5$)(0.010 mL, 0.095 mmol, 9.5 equivalents), and 0.5 mL of $CD_2Cl_2$ were placed in an NMR tube in the presence of $H_2$ (3 atm). After 5 hours at 22° C., 2.6 equivalents of $Et_2CHOH$ (3-pentanol) had formed, along with the ether $(Et_2CH)_2O$ (1.1 turnovers).

The results of the examples are summarized in Table 1:

TABLE 1

TEST RESULTS FOR THE HYDROGENATION OF 3-PENTANONE (DIETHYL KETONE) USING ORGANOMETALLIC TUNGSTEN (W) AND MOLYBDENUM (Mo) CATALYSTS

| Ex. No. | KETONE (mM)‡ | CATALYST/ (mM)‡ | SOLVENT (milliliter) | ALCOHOL (mM)‡/ turnovers | ETHER (mM)‡/ turnovers | TOTAL CATALYST TURNOVERS |
|---|---|---|---|---|---|---|
| 1 | 3-pentanone (300) | $[CpW(CO)_2(PPh_3)$ $(Et_2CO)]^+BAr'_4{}^-/(30)$ | $CD_2Cl_2$ | 3-pentanol (93)/3.1 | $(Et_2CH)_2O$ (5.7)/0.38 | 3.9 in 24 days |
| 2 | 3-pentanone (300) | $[CpW(CO)_2(PMe_3)$ $(Et_2CO)]^+BAr'_4{}^-/(30)$ | $CD_2Cl_2$ | 3-pentanol (69)/2.3 | none | 2.3 in 16 days |
| 3 | 3-pentanone (300) | $CpW(CO)_2(PCy_3)H/(30)$ and $Ph_3C^+BAr'_4{}^-/(30)$ | $CD_2Cl_2$ (0.7) | 3-pentanol (129)/4.3 | $(Et_2CH)_2O$ (2.2)/1.1 | 5.4 in 20 days |
| 4 | 3-pentanone (300) | $[CpMo(CO)_2(PPh_3)$ $(Et_2CO)]^+BAr'_4{}^-/(30)$ | $CD_2Cl_2$ (0.7) | 3-pentanol (236)/7.9 | $(Et_2CH)_2O$ (35)/2.4 | 10.3 in 5 days |
| 5 | 3-pentanone (300) | $[CpMo(CO)_2(PMe_3)$ $(Et_2CO)]^+BAr'_4{}^-/(30)$ | $CD_2Cl_2$ (0.7) | 3-pentanol (101)/3.4 | $(Et_2CH)_2O$ (25)/1.6 | 5 in 24 days |
| 6 | 3-pentanone (300) | $[CpW(CO)_2(PPh_3)$ $(Et_2CHOH)]^+BAr'_4{}^-/(30)$ | $CD_2Cl_2$ (0.7) | 3-pentanol (95)/3.2 | $(Et_2CH)_2O$ (7.6)/0.51 | 4.1 in 25 days |
| 7 | 3-pentanone (980) | $CpMo(CO)_2(PCy_3)H/(10)$ and $Ph_3C^+BAr'_4{}^-/(10)$ | $CD_2Cl_2$ (0.6) | 3-pentanol (220)/(22) | $(Et_2CH)_2O$ (30)/6 | 28 in 20 hours |
| 8 | 3-pentanone (190) | $[CpMo(CO)_2(PCy_3)$ $(CH_2Cl_2)]^+BAr'_4{}^-/(39)$ | $CD_2Cl_2$ (0.5) | 3-pentanol (160)/4.1 | $(Et_2CH)_2O$ (15)/0.8 | all in 2.5 hours |
| 9 | 3-pentanone (139) | $[CpW(CO)_2(PMe_3)$ $(H)_2)]^+BAr'_4{}^-/(39)$ | $CD_2Cl_2$ (0.72) | 3-pentanol (70)/1.8 | $(Et_2CH)_2O$ (6)/0.3 | 2. 1 in 15 days |
| 10* | 3-pentanone (95) | $CpMo(CO)_2(PCy_3)OTf/$ (34) | $CD_2Cl_2$ (2) | 3-pentanol (93)/2.7 | $(Et_2CH)_2O$ (2)/0.1 | 2.8 in 10 days |
| 11 | 3-pentanone (153) | $CpMo(CO)_2(PCy_3)(FBF_3)/$ (12) | $CD_2CL_2$ (0.62) | 3-pentanol (41)/3.4 | $(Et_2CH)_2O$ (2)/0.3 | 3.7 after 3 days |
| 12 | 3-pentanone (190) | $CpMo(CO)_2(PCy_3)H/(21)$ and $Ph_3C^+PF_6{}^-/(21)$ | $CD_2Cl_2$ (0.5) | 3-pentanol (55)/2.6 | $(Et_2CH)_2O$ (12)/1.1 | 3.7 after 5 hours |

Reactions were carried out at a temperature of 22° C. and an $H_2$ pressure of 3 atmospheres
‡mM is the concentration and is an abbreviation for millimoles per liter (mM is multiplied by the volume to obtain the number of moles (or millimoles).
*Example 10 used an $H_2$ pressure of 915 psi.
**For examples 1 and 6, 12 mM, 0.4 turnovers of $[CpW(CO)_2(PPh_3)(Et_2CHOH)]^+$ was also present.

Example 10

42.6 mg ($6.8 \times 10^{-2}$ mmol) of $CpMo(CO)_2(PCy_3)OTf$ and 0.020 mL (0.19 mmol, 2.8 equivalents) of 3-pentanone (diethyl ketone, $C_2H_5COC_2H_5$) were dissolved in 2 mL of a solution of $CD_2Cl_2$ in the presence of $H_2$ at a pressure of 915 psi. After 10 days at 22° C., >95% of the ketone had been hydrogenated, producing the alcohol $Et_2CHOH$ (3-pentanol) as the product, with only about 3% of the ether $(Et_2CH)_2O$.

Example 11

4.3 mg ($7.3 \times 10^{-3}$ mmol) of $CpMo(CO)_2(PCy_3)(FBF_3)$ was placed in an NMR tube, and 0.62 mL of a solution of $CD_2Cl_2$ and 0.010 mL (0.095 mmol) of 3-pentanone (diethyl ketone, $C_2H_5COC_2H_5$) were added in the presence of $H_2$ (3 atm). After 3 days 22° C, about 45% of the 3-pentanone had been hydrogenated, producing $Et_2CHOH$ (6 turnovers) and only trace (<5%) of the ether $(Et_2CH)_2O$.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

What is claimed is:

1. A process for the catalytic hydrogenation of an organic compound which contains at least one reducible functional group selected from the group consisting of R(C=O)R' and R(C=O)H, wherein R and R' are selected from hydrogen (H) or ay alkyl or aryl group, said process comprising reacting said organic compound with a catalyst in the presence of hydrogen, wherein said catalyst comprises an organometallic complex comprising a metal selected from the group consisting of tungsten and molybdenum, and wherein said organometallic complex is represented by the formula:

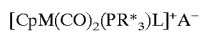

$$[CpM(CO)_2(PR^*_3)L]^+A^-$$

wherein Cp=$\eta^5$-R$^{\blacktriangle}_m$C$_5$H$_{5-m}$ and R$^{\blacktriangle}$ represents an alkyl group or a halogen (F, Cl, Br, I) or R$^{\blacktriangle}$=OR' (where R'=H, an alkyl group or an aryl group) or R$^{\blacktriangle}$=CO$_2$R' (where R'=H, an alkyl group or an aryl group) and m=0 to 5; M represents a molybdenum atom or a tungsten atom; R*$_3$ represents three hydrocarbon groups selected from a cyclohexyl group (C$_6$H$_{11}$), a methyl group (CH$_3$), and a phenyl group (C$_6$H$_5$) and all three R* groups can be the same or different or two of the three groups can be the same; L represents a ligand; and A$^-$ represents an anion.

2. The process for the catalytic hydrogenation of an organic compound according to claim 1, wherein said ligand is a weakly coordinated ligand.

3. The process for the catalytic hydrogenation of an organic compound according to claim 1, wherein said ligand is selected from the group consisting of said anion A$^-$, a hydrocarbon solvent molecule, a ketone substrate molecule, a product alcohol molecule and a C=C bond of a PPh$_3$ ligand.

4. The process for the catalytic hydrogenation of an organic compound according to claim 1, wherein said anion (A$^-$) is selected from the group consisting of PF$_6^-$, BF$_4^-$, PF$_6^-$, CF$_3$SO$_3^-$ and BAr'$_4^-$, wherein Ar'=3,5-bis (trifluoromethyl) phenyl.

5. The process for the catalytic hydrogenation of an organic compound according to claim 3, wherein said solvent molecule is selected from the group consisting of dichloromethane (CH$_2$Cl$_2$), toluene (C$_6$H$_5$CH$_3$), chlorobenzene (ClC$_6$H$_5$), and trifluorotoluene (CF$_3$C$_6$H$_5$).

6. The process for the catalytic hydrogenation of an organic compound according to claim 3, wherein said solvent molecule is said organic compound that is being hydrogenated.

7. The process for the catalytic hydrogenation of an organic compound according to claim 1, wherein said R and R' are selected from an alkyl group.

8. The process for the catalytic hydrogenation of an organic compound according to claim 1, wherein said R and R' are selected from an aryl group.

9. The process for the catalytic hydrogenation of an organic compound according to claim 1, wherein said R is selected from an alkyl group and R' is selected from an aryl group.

10. The process for the catalytic hydrogenation of an organic compound according to claim 1, wherein said R is selected from an aryl group and R' is selected from an alkyl group.

11. The process for the catalytic hydrogenation of an organic compound according to claim 1, wherein said process is carried out at a pressure of from about 1 atmosphere to about 3 atmospheres.

12. The process for the catalytic hydrogenation of an organic compound according to claim 1, wherein said process is carried out at a temperature of from about -95° C. to about 60° C.

13. The process for the catalytic hydrogenation of an organic compound according to claim 1, wherein said process is carried out at a pressure of from about 1 atmosphere to about 3 atmospheres and at a temperature of from about -95° C. to about 60° C.

* * * * *